US006852992B2

(12) United States Patent
Takezawa et al.

(10) Patent No.: US 6,852,992 B2
(45) Date of Patent: Feb. 8, 2005

(54) METHOD AND APPARATUS OF DIAGNOSING DETERIORATION OF AN ARTICLE

(75) Inventors: Yoshitaka Takezawa, Hitachinaka (JP); Jun'ichi Katagiri, Naka (JP); Hiroshi Shoji, Hitachi (JP); Kenichi Ootaka, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 288 days.

(21) Appl. No.: 10/082,282

(22) Filed: Feb. 26, 2002

(65) Prior Publication Data

US 2003/0001119 A1 Jan. 2, 2003

(30) Foreign Application Priority Data

Jun. 29, 2001 (JP) ........................................ 2001-197654

(51) Int. Cl.[7] .............................................. G01N 21/88
(52) U.S. Cl. ............... 250/559.45; 250/225; 356/237.1; 356/364
(58) Field of Search ........................... 250/225, 559.45; 356/237.1, 364, 432

(56) References Cited

U.S. PATENT DOCUMENTS 3,904,293 A * 9/1975 Gee ........................... 356/369
6,169,601 B1 * 1/2001 Eremin et al. ............ 356/239.8
6,307,627 B1 * 10/2001 Vurens ........................ 356/369

FOREIGN PATENT DOCUMENTS

| JP | 7-35732 | 2/1995 | | |
|---|---|---|---|---|
| JP | 7-245869 | 9/1995 | | |
| JP | 9-2222393 | 8/1997 | | |
| JP | 10-19856 | 1/1998 | | |
| JP | 10-115601 | * 5/1998 | .......... | G01N/29/00 |
| JP | 11-118773 | * 4/1999 | .......... | G01N/29/10 |
| JP | 11-235097 | * 8/1999 | ............ | H02P/9/00 |
| JP | 11-330185 | 11/1999 | | |
| JP | 2000-131243 | 5/2000 | | |

OTHER PUBLICATIONS

T. Ikeda et al, "Development of the Ultrasonic Degradation Tester for Low Voltage Cables", Transactions of the Institute of Electrical Engineers of Japan, vol. 120–B, No. 11, pp. 1437–1442, 2000.

* cited by examiner

*Primary Examiner*—David Porta
*Assistant Examiner*—Davienne Monbleau
(74) *Attorney, Agent, or Firm*—Mattingly, Stanger & Malur, P.C.

(57) ABSTRACT

Light having polarization is irradiated onto an article, and then quality of the article is diagnosed using a pre-input correlation function between quality of the article and a variation of polarization of the light reflected from the article. Further, the quality of the article is diagnosed by measuring a reflection absorbance difference or a reflection absorbance ration of light from the article between two wavelenghts, and by measuring a depolarization degree of polarized light of the reflected light from the surface of the article. The quality of the article can be non-destructively diagnosed using a simple system. Further, defects can be identified of factor-by-factor basis.

6 Claims, 10 Drawing Sheets

| AREA 1<br>TEMPERATURE : 55°C<br>RADIATION DOSE :<br>$1.0 \times 10^{-2}$ Gy/h | KIND OF CABLE | NUMBER OF CABLES | NUMBER OF MEASURED CABLES |
|---|---|---|---|
| | POWER CV CABLE | 23 | 10 |
| | CONTROL CV CABLE | 117 | 18 |
| | INSTRUMENT CV CABLE | 56 | 10 |
| | CONTROL KGB CABLE | 7 | 7 |

| AREA 2<br>TEMPERATURE : 40°C<br>RADIATION DOSE :<br>$1.0 \times 10^{-4}$ Gy/h | KIND OF CABLE | NUMBER OF CABLES | NUMBER OF MEASURED CABLES |
|---|---|---|---|
| | POWER CV CABLE | 23 | 10 |
| | CONTROL CV CABLE | 230 | 23 |
| | INSTRUMENT CV CABLE | 106 | 11 |
| | CONTROL VV CABLE | 51 | 10 |

| AREA 3<br>TEMPERATURE : 65°C<br>RADIATION DOSE : 2.0Gy | KIND OF CABLE | NUMBER OF CABLES | NUMBER OF MEASURED CABLES |
|---|---|---|---|
| | POWER PN CABLE | 18 | 10 |
| | CONTROL PN CABLE | 32 | 10 |
| | INSTRUMENT PN CABLE | 28 | 10 |

FIG. 12

METHOD AND APPARATUS OF DIAGNOSING DETERIORATION OF AN ARTICLE

BACKGROUND OF THE INVENTION

The present invention relates to an evaluation method of evaluating an article, a deterioration diagnosis system for diagnosing a deterioration degree using the evaluation method, a material identification system for identifying an internal material and a quality control system for controlling quality.

A technology of controlling quality of an article by irradiating light on the article to diagnose the physical properties is widely used. The diagnosis of an article by irradiating light on the article and measuring the reflected light is preferable because the diagnosis is affected by an internal material of the article, and the article need not to be contaminated or damaged.

For example, a semiconductor device is required to have high smoothness of its surface. Japanese Patent Application Laid-Open No.11-330185 discloses an apparatus for manufacturing semiconductor devices in which polarized light is irradiated onto the semiconductor device to evaluate a surface state or a film thickness of a semiconductor layer. Further, Japanese Patent Application Laid-Open No.2000-131243 discloses an optical sensor which detects a surface state of an object to be detected by accurately evaluating and correcting a distance between the object to be detected and the measurement instrument. In these optical diagnoses, asperities on the surface are detected by measuring phase difference between incident light and reflected light to accurately measure the phase of polarized light.

Japanese Patent Application Laid-Open No.11-235097 and Japanese Patent Application Laid-Open No.9-222393 propose a deterioration diagnosis system which diagnoses a deterioration degree by measuring a reflection absorbance difference between or a reflection absorbance ratio of two light beams each having an arbitrary wavelength among light beams irradiated on an object from plural kinds of monochromatic light sources, and by referring the relationship between the absorbance difference or the absorbance ratio and deterioration degree.

In addition, Japanese Patent Application Laid-Open No.10-115601 discloses deterioration diagnosis of an insulator coated film in which elastic wave is measured by irradiating light on the insulator coated film.

There are many kinds of physical properties in an article required to be diagnosed. Therefore, in the evaluation methods described above, there exist some physical properties which are not evaluated.

Since needs of miniaturization and close-packing of semiconductor devices are being increased, a technology capable of diagnosing defects in a material composing a product in addition to smoothness of the surface of the material is required in the field of the semiconductor device manufacturing. The technology evaluating materials is useful because the technology can be used for not only the semiconductor device but also for controlling quality of articles. The present invention has been made under the background described above.

Further, in the deterioration diagnosis system described above, deterioration factors not appearing change in the reflection absorbance or the reflection absorbance ratio cannot be diagnosed by the deterioration diagnosing method described above. In regard to deterioration of an article, there are many deterioration factors depending on an environment where the article is placed. For example, for a cable installed in a facility relating to a nuclear power station, the deterioration factors are heat and radiation dose, and the deterioration may progress faster compared to a cable placed in the other facilities. Since the electric insulating property of the cable is degraded by deterioration, it is necessary to change the cable before the deterioration is progressed. There are many reports since there is a large demand for the deterioration diagnosis of cables. Deterioration diagnoses of cable sheathing insulator materials utilizing ultrasonic wave propagation speed are disclosed in Japanese Patent Application Laid-Open No.11-118773, Japanese Patent Application Laid-Open No.10-19856 and Japanese Patent Application Laid-Open No.7-35732. Deterioration diagnosis of insulation materials by detecting small leakage current is disclosed in Japanese Patent Application Laid-Open No.7-245869. In connection with these diagnosis methods, it is described in the Transaction of the Institute of Electrical Engineers of Japan, vol.120-B, No.11, p1437 (2000) that an index of deterioration state is generally expressed by the correlation with elongation characteristic.

Therefore, it is desirable to execute a highly reliable deterioration diagnosis by studying a factor of material deterioration and selecting a method corresponding to the factor.

Further, as described above, progress of deterioration of an article depends on the surrounding environmental condition. Further, when the deterioration diagnosis of cables is performed, in a case where a large amount of cables are laid like in a power station, it is difficult to measure all the cables having different laying time and different laying environment.

SUMMARY OF THE INVENTION

An object of the present invention is to provide a method of diagnosing quality of an object to be diagnosed corresponding to a defect factor of the object to be diagnosed.

A further object of the present invention is to provide a deterioration managing method which determines a changing timing and a handling method of deteriorated articles.

A first means for solving the above-described problem is a quality diagnostic system which irradiates light having polarization onto a article, and measures a variation of polarized light of the reflected light from the article, and diagnoses the quality of the article using a pre-input correlation between quality of the article and variation of polarized light.

Further, the first means for solving the above-described problem is a material identifying method in which light having polarization is irradiated onto an article, and a variation of polarized light of the reflected light from the article is measured to detect the material of the article from the variation of polarized light.

A second means for solving the above-described problem is a deterioration diagnostic system in which light having polarization is irradiated onto an article, and a depolarization degree of the reflected light from the article is measured, and then the degradation of the article is diagnosed using a pre-stored correlation function between deterioration degree of the article and depolarization degree of polarized light.

Further, a third means for solving the above-described problem is a method in which light having polarization is irradiated onto an article, a first deterioration degree of the article being measured using a depolarization degree of polarized light of the reflected light, light having a plurality of arbitrary wavelengths being irradiated onto the article, the reflected light from the article being measured, a second deterioration degree of the article being measured using a reflected light intensity difference (including absorbance difference or absorbance ratio) between the arbitrary two wavelengths, then a deterioration degree of the article being diagnosed using the first deterioration degree and the second deterioration degree.

A fourth means for solving the above-described problem is a deterioration managing method in which polarized light is irradiated onto an article, the reflected light of the polarized light being received, a depolarization degree of the polarized light being measured, a deterioration degree of the article being diagnosed using a correlation function between the depolarization degree of the polarized light and the deterioration degree of the article, and then a changing timing of the article being determined. In a case where there are many articles of which their deterioration degrees are to be diagnosed, arbitrary articles among all the articles are diagnosed. Then, if it is judged that some articles are necessary to be changed, all the articles are changed. Thereby, management of many articles can be performed.

A fifth means for solving the above-described problem is a deterioration managing method in which polarized light is irradiated onto an article, the reflected light of the polarized light being received, a depolarization degree of the polarized light being diagnosed, a first deterioration degree of the article being diagnosed using a correlation function between the depolarization degree of the polarized light and the deterioration degree of the article, light having a plurality of wavelengths being irradiated onto the article, an absorbance difference or an absorbance ratio of the light having the plurality of wavelengths being measured, a second deterioration degree of the article being diagnosed using a correlation function between the variation of light intensity and the deterioration degree of the article, a deterioration factor being identified from the first deterioration degree and the second deterioration degree, then a method of coping with the deterioration factor being output.

The deterioration factor of the article is identified, and an action for excluding the deterioration factor such as change of the installation place of the article or change of the material of the article is made. As the result, the deterioration is suppressed to improve the durability of the system and accordingly to reduce the cost.

DESCRIPTION OF THE PREFERRED EMBODIMENTS

The present invention will be described below in detail.

The inventors of the present invention studied on the relationship between deterioration degrees and optical properties of various kinds of cable sheathing insulation materials. As the result, it was clarified that polarization of reflected light from the surface of the cable sheathing insulator material was varied as the deterioration was progressed. Further, the inventors of the present invention found that the variation was different in the deterioration factor from variation in the reflection absorbance difference or the reflection absorbance ratio. By combining the variation of polarization due to deterioration of the cable sheathing insulation material and the variation of the reflection absorbance difference or the reflection absorbance ratio of light between two wavelengths, the deterioration degrees of the cable sheathing insulation material can be determined on a factor-by-factor basis.

Therein, a light intensity ratio of the minor axis to the major axis of polarized light can be used as the variation of polarization.

The correlation function between the deterioration degree of the article and the depolarization degree of the polarized light may be formed by artificially deteriorating an article or may be formed by measuring the depolarization degree of polarized light of a naturally deteriorated article.

(1) A non-destructive deterioration diagnostic method and a non-destructive deterioration diagnostic system according to the present invention are characterized by that irradiation light having polarity from a light source emitting light having at least one kind of wavelength is irradiated onto a surface of the article; the reflected light from the article being received; a depolarization degree (DP) of polarized light of reflected light being measured; a first deterioration degree of the article being determined by executing comparison operation using a prestored relationship between depolarization degrees of polarized light and deterioration degrees formed using a deteriorated material of the same kind as a material of the article; irradiation light having at least two kinds of wavelengths being irradiated onto the surface of the article; the at least two kinds of reflected light from the article being received; an intensity of the reflected light for each wavelength ($I_\lambda$) being measured at a light quantity measurement portion; a reflection absorbance ($A_\lambda$)

being calculated by Equation (1); a reflection absorbance difference (ΔA) or a reflection absorbance ratio (A') of two arbitrary wavelengths being calculated by Equation (2) or Equation (3); a second deterioration degree of the article being determined by executing comparison operation using a pre-stored relationship between reflection absorbance difference or reflection absorbance ratio and deterioration degree formed using an artificially deteriorated material of the same kind as a material of the article; and finally a comprehensive deterioration degree of the article being determined from the determined results of the first deterioration degree and the second deterioration degree based on a pre-stored relationship.

$$A_\lambda = -\log(I_\lambda/I_0) \quad (1)$$

(there, $I_0$ is reference reflected light intensity)

$$\Delta A = (A_{\lambda 1}) - (A_{\lambda 2}) \quad (2)$$

(there, $\lambda 1 < \lambda 2$)

$$A' = (A_{\lambda 1})/(A_{\lambda 2}) \quad (3)$$

(there, $\lambda 1 < \lambda 2$)

Therein, as the light source, either of a monochromatic light source having a peak wavelength in an arbitrary wavelength (for example, above 400 nm and below 1350 nm) or a light source extracting light using an interference filter from a white light source such as a halogen lamp may be used. Further, as the monochromatic light source, a laser diode (LD) or a light-emitting diode (LED) is preferable because of easy availability, long lifetime and stable performance. The light source for measuring the reflection absorbance difference or the reflection absorbance ratio and the light source for measuring the DP may use either the same wavelength light or different wavelength light.

Further, the method of irradiating light onto the surface of the article may be performed by directly irradiating light from the light source through an optical system composed of an optical lens group or by irradiating through an optical fiber. In regard to the optical fiber cable, although the measurement can be performed by using a single optical fiber wire, in order to increase a quantity of light and to reduce bending loss it is preferable to use a bundle fiber formed by bundling optical fiber wires. Further, when an optical fiber is used as the light guiding body for measuring the DP, polarization plane preserving fiber should be used. A polarizer is generally used to extract polarized light, and an analyzer is also used for measuring the DP.

(2) The non-destructive deterioration diagnosis described above can be applied to the diagnosis for cable coating insulation material. In this case, the non-destructive deterioration diagnosis can be applied to a cable management method for determining changing timing of deteriorated cables. A deterioration management method for cable coating insulation material according to the present invention is characterized by that the method comprises the steps of obtaining a relationship between physical property and/or electric characteristic of each material used for a cable sheathing insulation material and optical diagnosis result obtained from the non-destructive deterioration diagnosis method of cable sheathing insulation material; inputting data on the sheathing insulator material and manufacturing time of a laid cable to be diagnosed, and laying and environment data such as laying time, a place of the cable laying, a laying period and measuring position information to set a deterioration control value for determining a changing timing for each material of the cable sheathing insulation material using the data group for diagnosis in advance; and determining a changing timing of the cable by executing comparison operation between an optical diagnosis result of the sheathing insulation material of the cable to be diagnosed and the preset deterioration control value.

Figure 6:
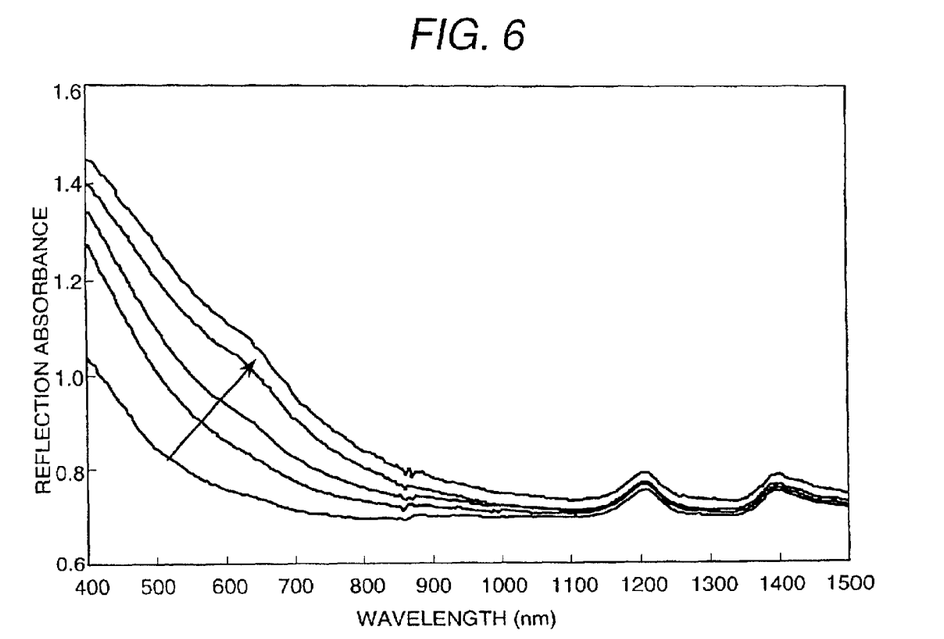
FIG. 6 is a graph showing an example of change in reflection absorbance spectrum of a cable sheathing insulation material.

In general, the change of reflection absorbance spectrum of a cable coating insulation material caused by deterioration can be typically expressed by the change shown in FIG. 6. The reflection absorbance spectra are not influenced by measuring temperature or by humidity. Since the reflection absorbance in the short wavelength side is increased as the deterioration is progressed as shown in the figure, the coating insulation material is gradually changed dark-colored. The increase in the spectrum in the short wavelength side is mainly caused by change in the chemical structure (bonding form) due to thermal oxidation deterioration of the resin, and in solid-state physics, caused by increase in the electronic transition absorption loss. Since the behavior described above is exhibited, the reflection absorbance difference and the reflection absorbance ratio between arbitrary two wavelengths are similarly changed with progress of deterioration. The reason why the difference or the ratio between the two wavelengths is taken is to cancel the effect of the surface state. In the present invention, the progress degree of deterioration mainly caused by the chemical structure (bonding form) change is to be referred to a second deterioration degree.

In the cable laid in a facility relating to a nuclear power station or the like, progress of the deterioration of the cable is sometimes faster than that of cables laid in the other common environment. It is considered that the reason to accelerating the deterioration is change in higher structure of resin, that is, crystallization (coagulation) of resin inner portions. Since the change in the higher structure does not cause the change in the chemical structure (bonding form), the change in the higher structure cannot be found by the reflection absorbance spectrum described above. In order to find the change in the higher structure, that is, the change in the crystallization, the present invention employs a measuring method using polarized light. A depolarization degree of polarized light is quantitatively measured through polarization measurement, and a variation of the higher structure can be correlated with a deterioration degree using a separately generated calibration curve. Therein, in the present invention, the progress degree of deterioration mainly caused by the higher structure (crystallization) change is to be referred to a first deterioration degree.

As described in Japanese Patent Application Laid-Open No.3-226651, a deterioration degree is generally expressed by a reduced time θ. By expressing by the reduced time θ, even if materials have various kinds of deterioration histories, the deterioration degrees the materials are equal to each other when the reduced time is the same. The reduced time θ is defined by Equation (4).

$$\theta = t \times \exp(-\Delta E/RT) \quad (4)$$

where, $\Delta E$ is an apparent activation energy of deterioration (J/mol), R is the gas constant (J/K/mol), T is an absolute temperature of deterioration (K), and t is a deterioration time (h).

The apparent activation energy of deterioration $\Delta E$ can be easily calculated by artificially deteriorating a material of the same kind and forming Arrhenius plots of the results. Further, letting a reduced time corresponding to a pre-set lifetime be $\theta_0$, a difference $\Delta\theta$ between the reduced life time $\theta_0$ and a reduced time θ obtained from actual measurement is a reduced time corresponding to a residual lifetime which is used as a reference for judging the deterioration degree. That is, the residual lifetime Δt (h) can be expressed by Equation (5).

$$\Delta t = \Delta \theta / \exp(-\Delta E/RT) \qquad (5)$$

When the condition of an average using temperature after time t is determined, the residual lifetime Δt (=$t_0$-t) can be calculated.

The progress degrees of deterioration are calculated based on individual deterioration judging references, and then in the actual judgment, a result of progressed deterioration is derived as the true deterioration degree from both of the calculated deterioration degrees. Since the present diagnosis can evaluate both of the chemical structure (bonding form) change and the higher structure (crystallization degree) change at a time, it is possible for the first time to perform comprehensive diagnosis capable of including change in values of the other physical properties which have failed to be noticed by the conventional evaluation technologies paying attention on only one physical property. As described above, in the present invention the deterioration degree can be diagnosed on each deterioration basis. Further, since the deterioration degree is judged by measuring the reflected light from the surface, the characteristics of the base resin itself can be easily measured, and the measurement is hardly affected by the kind and the mixing amount of the plasticizer or the filler which exists in the inner portion and not appears on the surface.

As described above, the higher structure of resin or the like can be evaluated by measuring the depolarization degree of polarized light. In a case where there is a portion having a different higher structure in a material of an article, is possible to detect the portion be irradiating polarized light on the article and measuring the depolarization degree of the polarized light as described above. By utilizing this characteristic, it is possible to control quality of an article or to evaluate a material of an article using the diagnostic system as described above.

The present invention will be described below in detail, referring to embodiments.

(Embodiment 1)

Figure 1:
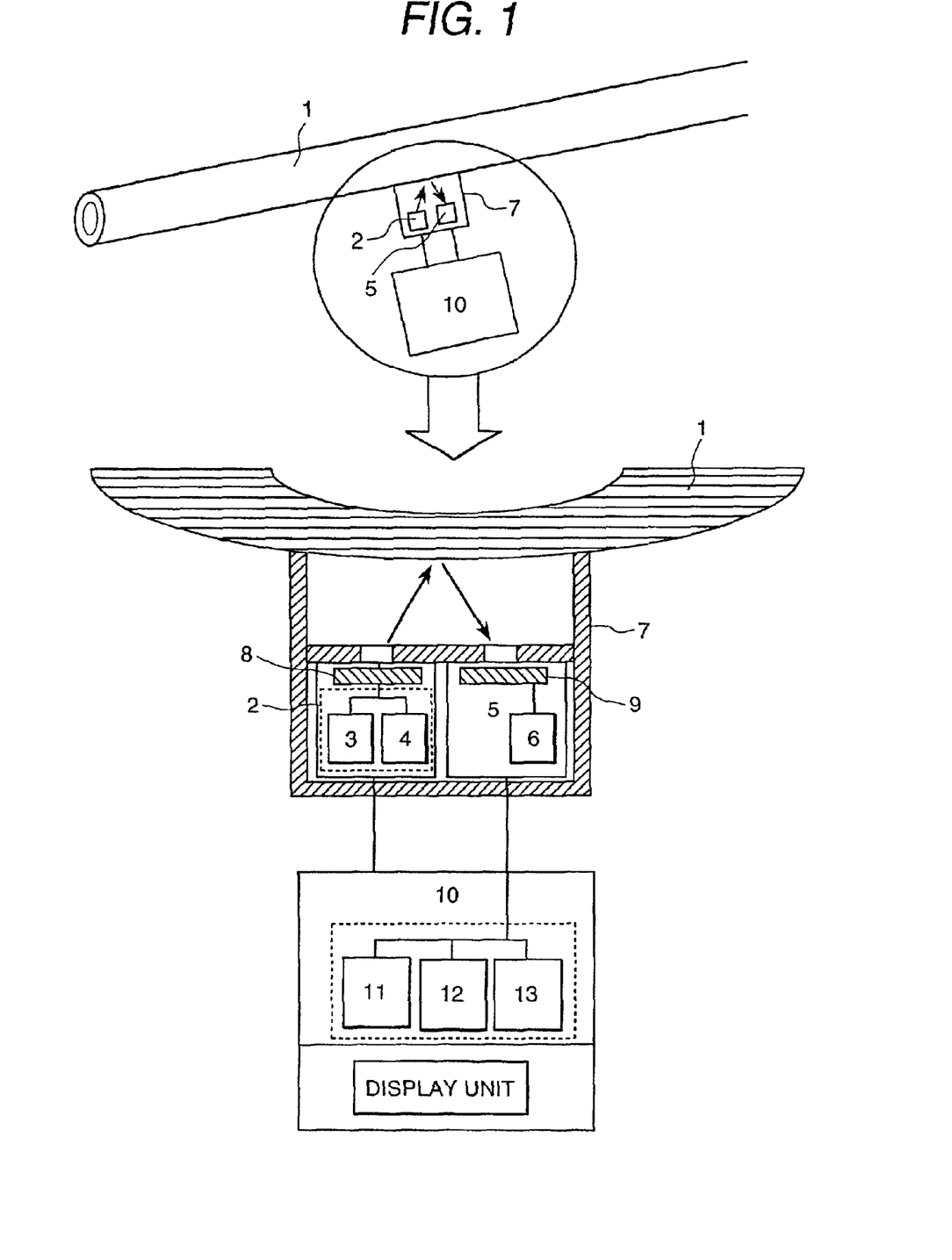
FIG. 1 is a block diagram showing an embodiment of a non-destructive diagnosis system for cable sheathing insulation material in accordance with the present invention.
Figure 2:
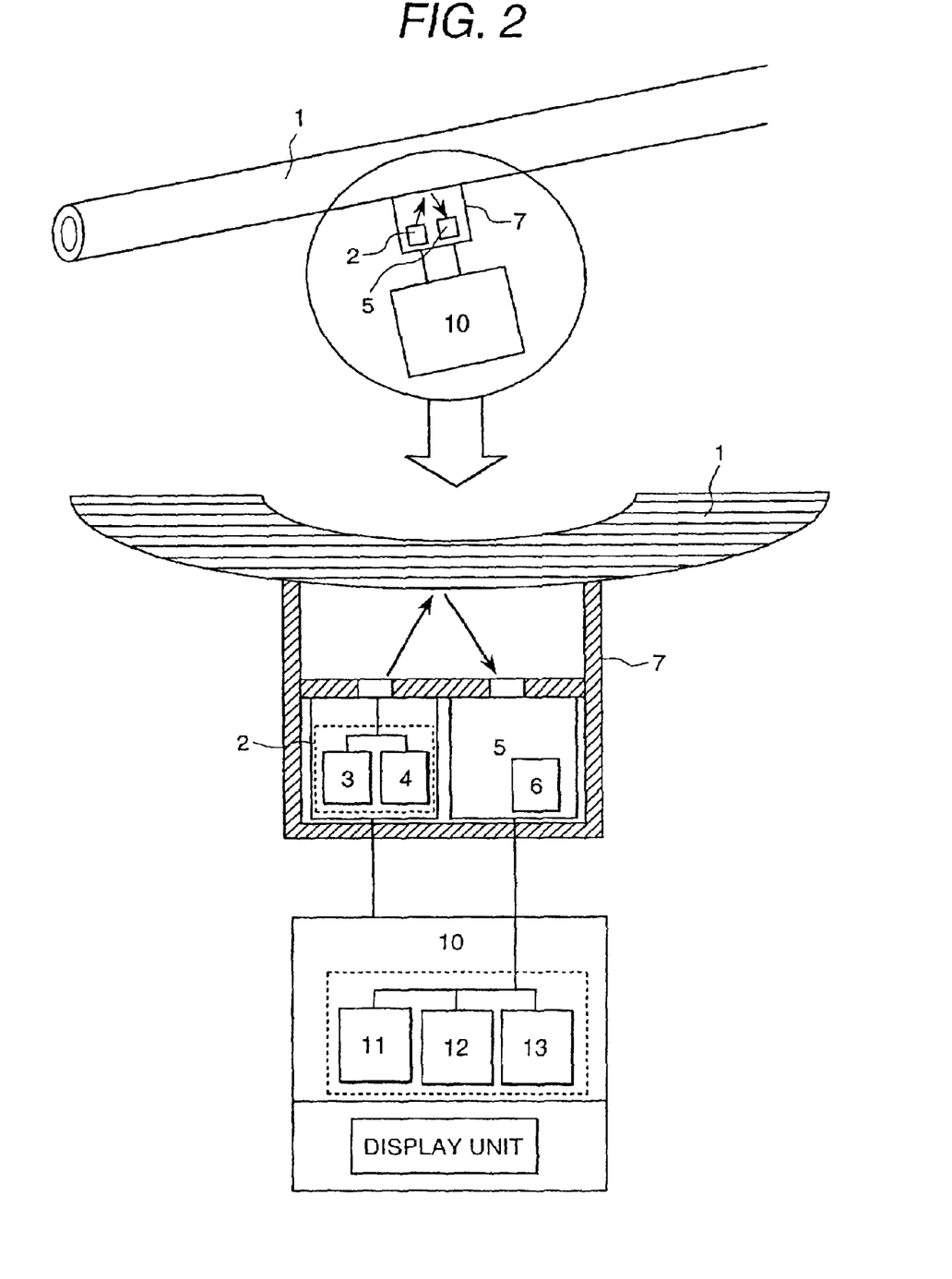
FIG. 2 is a block diagram showing an embodiment of a non-destructive diagnosis system for cable sheathing insulation material in accordance with the present invention.
Figure 3:
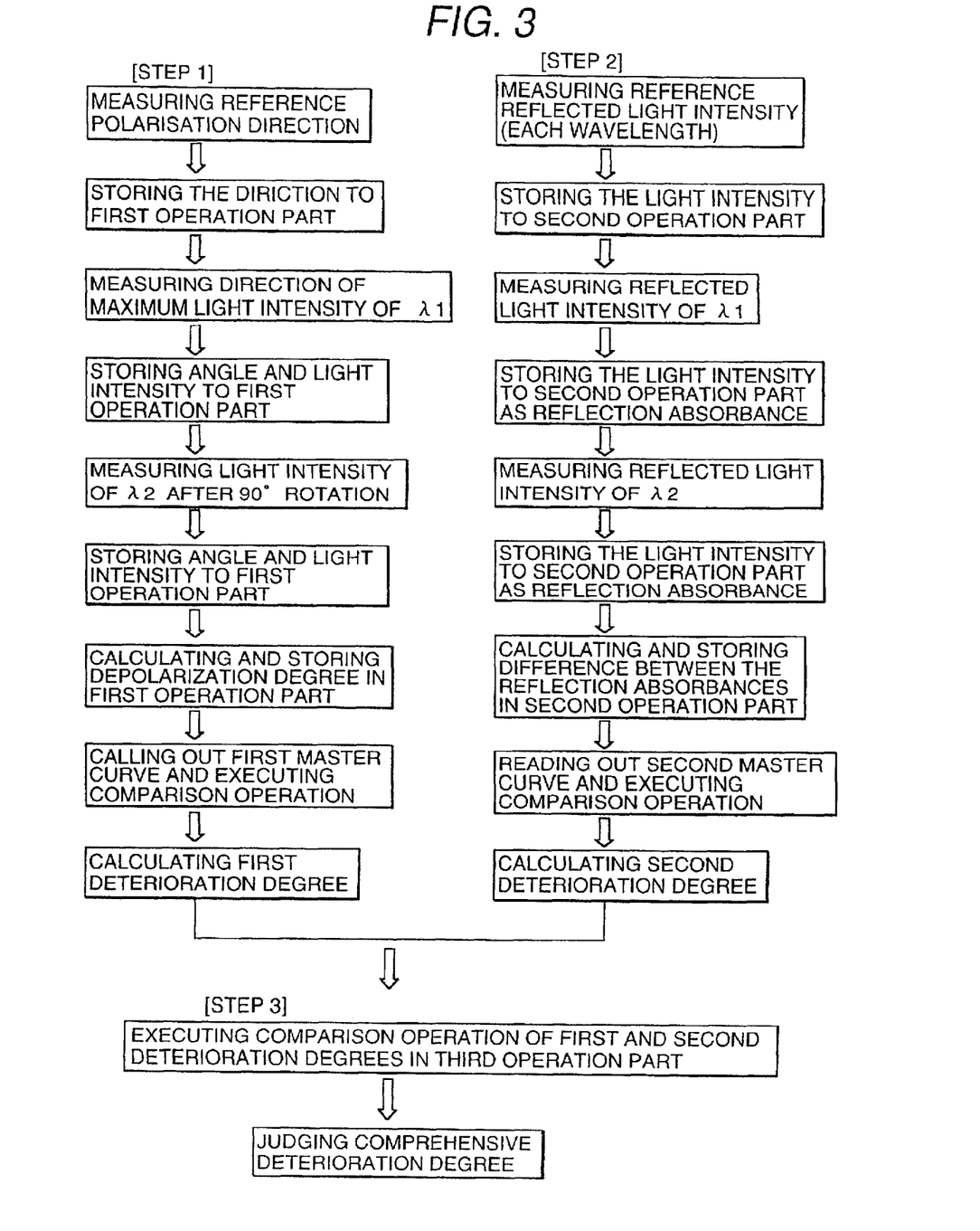
FIG. 3 is a flowchart of calculation for determining a deterioration degree using depolarization degree and absorbance difference.

FIG. 1 and FIG. 2 is a block diagram showing an embodiment of a non-destructive diagnosis system for cable sheathing insulation material in accordance with the present invention. FIG. 3 is a flowchart of calculation for determining a deterioration degree. These figures illustrate deterioration diagnosis of a cable coating insulation material. Referring to FIG. 1 and FIG. 2, an operation part 11, an operation part 12 and an operation part 13 are composed of a hard disk unit, a measured data storing memory, a read-only memory, a microprocessor, a display unit and so on, and perform not only calculation of the deterioration degree but also perform switching of light source wavelength, inserting and withdrawing of a polarizer 8 and an analyzer 9, driving control of the analyzer, and displaying an operation results. As light sources of a light source portion 2, a laser diode (LD) of λ1=405 nm and a laser diode (LD) of λ2=780 nm were used in a condition of 400 μW emitting light output power, respectively.

Figure 5:
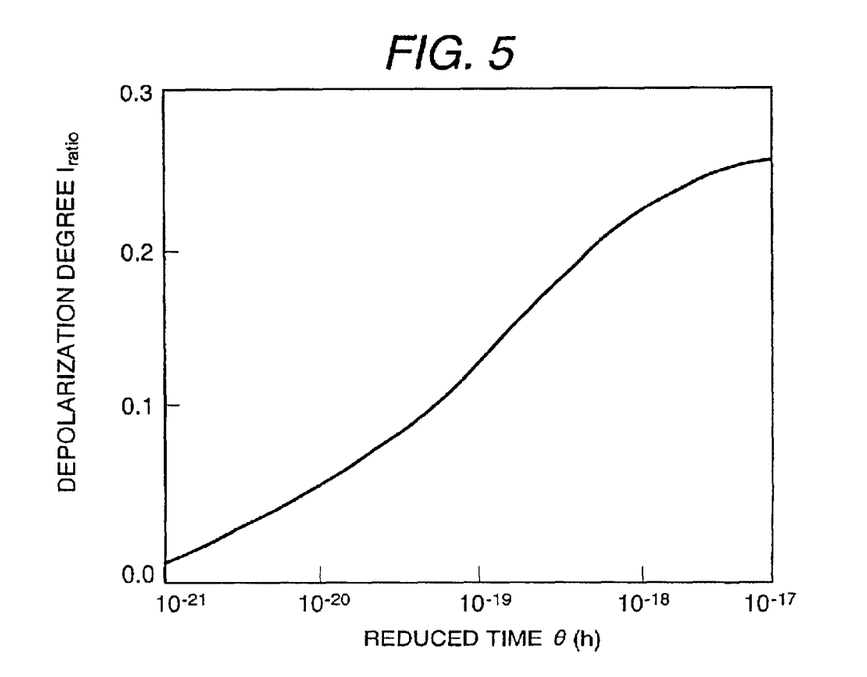
FIG. 5 is a graph showing an example of the relationship between depolarization degree (DP) and deterioration degree (a first master curve).

Initially, description will be made below on the method of evaluating the depolarization degree (DP) of the polarized light by measuring polarized light of the reflected light of the cable coating insulation material 1, referring to FIG. 1. Firstly, the operation part 12 outputs an instruction of inserting the polarizer 8 and the analyzer 9 to insert filters to the light source portion 2 and a detector 6. A rotating mechanism for detecting a rotation of a plane of polarization due to the measured sample is contained in the analyzer 9, and the operation part 12 also executes driving control of the rotating mechanism. In the present embodiment, light measurement using the light source of λ2 was performed. In order to determine a reference angle $\alpha_0$, before starting actual measurement, pre-measurement is performed using an alumina white plate or the like and, the result is pre-set to the operation part. The polarized emitted light from the light source of λ2 is reflected on the surface of the cable coating insulation material 1 to reach the detector 6 through the analyzer 9. The analyzer is driven by a servo motor until the quantity of light becomes the maximum value, and the angle α and the light intensity $I_\alpha$ at that time are obtained. Therein, a distance between the surface of the cable coating insulation material 1 and the end surface (including a protective quartz glass plate) of the light source portion 2 is 3 mm. Next, the analyzer 9 is rotated to a position of an angle larger than α by +90° to measure a light intensity $I_{90}$ at that position. In the present invention, $I_{ratio}=I_{90}/I_\alpha$ is used as the index of DP. The first deterioration degree is determined from the value $I_{ratio}$ obtained as described above. The measured result in this time was $I_{ratio}=0.11$. Further, a relationship (a master curve) between the depolarization degree (DP) of the polarized light and the deterioration degree of the cable coating insulation material 1 shown in FIG. 5 is pre-stored in the operation part 12, the measured deterioration degree of the cable coating insulation material can be calculated as the reduced time θ using the relational chart to display the result. Since the ratio $I_{ratio}$ at the lifetime point in the case of the cable coating insulation material in this time is 0.24, the progress degree of the deterioration is 46%. In other words, it can be understood that the deterioration is progressed by 46% as change in the higher structure (crystallization degree).

Figure 4:
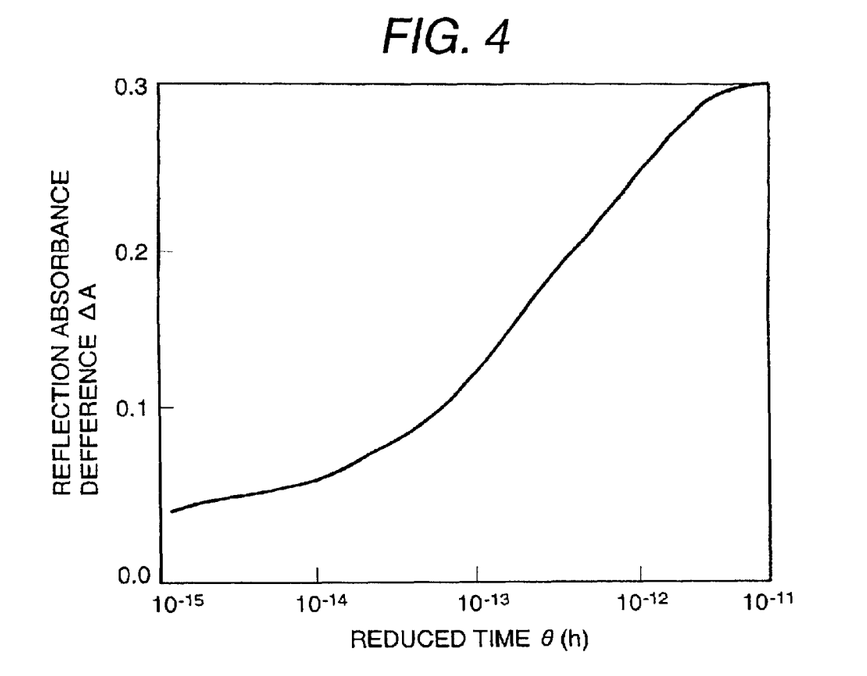
FIG. 4 is a graph showing an example of the relationship between reflection absorbance difference and deterioration degree (a second master curve).

Next, description will be made below on the method of evaluating the absorbance difference or the absorbance ratio by measuring light intensities of the reflected light of the cable coating insulation material 1, referring to FIG. 2. The reflected light intensities ($I_{\lambda 1}$, $I_{\lambda 2}$) of the cable coating insulation material 1 of the light sources of the individual wavelengths were measured as flows. The emitted light from the light source of λ1 is reflected on the surface of the cable coating insulation material 1 to reach the light quantity measuring portion 5, and the light intensity $I_{\lambda 1}$ is obtained. Therein, a distance between the surface of the cable coating insulation material 1 and the end surface (including a protective quartz glass plate) of the light source portion 2 is 3 mm. There, an optical system is set so that the irradiating light beams of the two wavelengths of λ1 and λ2 emitted from the light source portion 2 are irradiated onto the same area on the surface of the cable coating insulation material 1. The operation part 11 calculates the reflection absorbance in the wavelength λ1 using Equation (1) to store $A_{\lambda 1}$. Therein, the reference reflection light intensity I0 for each wavelength has been measured using an alumina white plate and pre-set to the operation part before starting the measurement. Similarly, the reflection light intensity $I_{\lambda 2}$ of the cable coating insulation material 1 to the emitted light from the light source λ2 is measured, and the reflection absorbance $A_{\lambda 2}$ for the light of wavelength λ2 is stored in the operation part 11. The reflection absorbance difference ΔA between the two wavelengths is calculated from the values of reflection absorbance $A_{\lambda 1}$ and $A_{\lambda 2}$ of the cable coating insulation material 1 to the wavelengths λ1 and λ2 using Equation (2). Since the measured results in this time were $I_{0,\lambda 1}=2.22$ μW, $I_{0,\lambda 2}=2.35$ μW, $I_{\lambda 1}=1.15$ μW and $I_{\lambda 2}=1.95$ μW, the reflection absorbance difference ΔA became 0.205 from Equation (1) and Equation (2). Further, a relationship (a master curve) between the reflection absorbance difference and the deterioration degree of the cable coating insulation material 1 shown in FIG. 4 is pre-stored in the operation part 11, the measured deterioration degree of the cable coating insulation material can be calculated as the reduced time θ using the relational chart to display the result. Since the reduced time $\theta_0$ at the lifetime point in the case of the cable coating insulation material in this time is 0.30, the progress degree of the deterioration is 68%. In other words, it can be understood that the deterioration is progressed by 68% as change in the chemical structure (bonding form).

Finally, in the operation part 13, the comprehensive deterioration degree of the cable coating insulation material 1 is determined from the first deterioration degree (46%) and the second deterioration degree (68%) obtained as described above based on a pre-stored relationship. The present embodiment employed a relational equation which determines a value of the further progressed deterioration degree as the comprehensive deterioration degree in the safety side by comparing the first deterioration degree and the second deterioration degree. As the result, the value of the second deterioration degree (68%) is obtained as the final result of the deterioration degree. That is, when the chemical structure (bonding form) change and the higher structure (crystallization degree) change are evaluated in the factor-by-factor basis, it can be judged that in the cable coating insulation material, progress of the deterioration caused by the chemical structure (bonding form) change is large. As described above, it is possible to perform comprehensive diagnosis capable of including change in values of the other physical properties which have failed to be noticed by the conventional evaluation technologies paying attention on only one physical property. As described above, in the present invention the deterioration degree can be diagnosed on each deterioration basis.

In a case of diagnosing a cable insulator, the diagnosis can be performed using the cable insulator instead of the cable coating insulation material 1.

(Embodiment 2)

Description will be made below on a diagnostic system using optical fiber cables for the light guide passages in a method similar to that of Embodiment 1. As light sources of a light source portion 2, a laser diode (LD) of λ1=405 nm and a laser diode (LD) of λ2=1310 nm were used in a condition of 900 μW emitting light output power, respectively.

Figure 8:
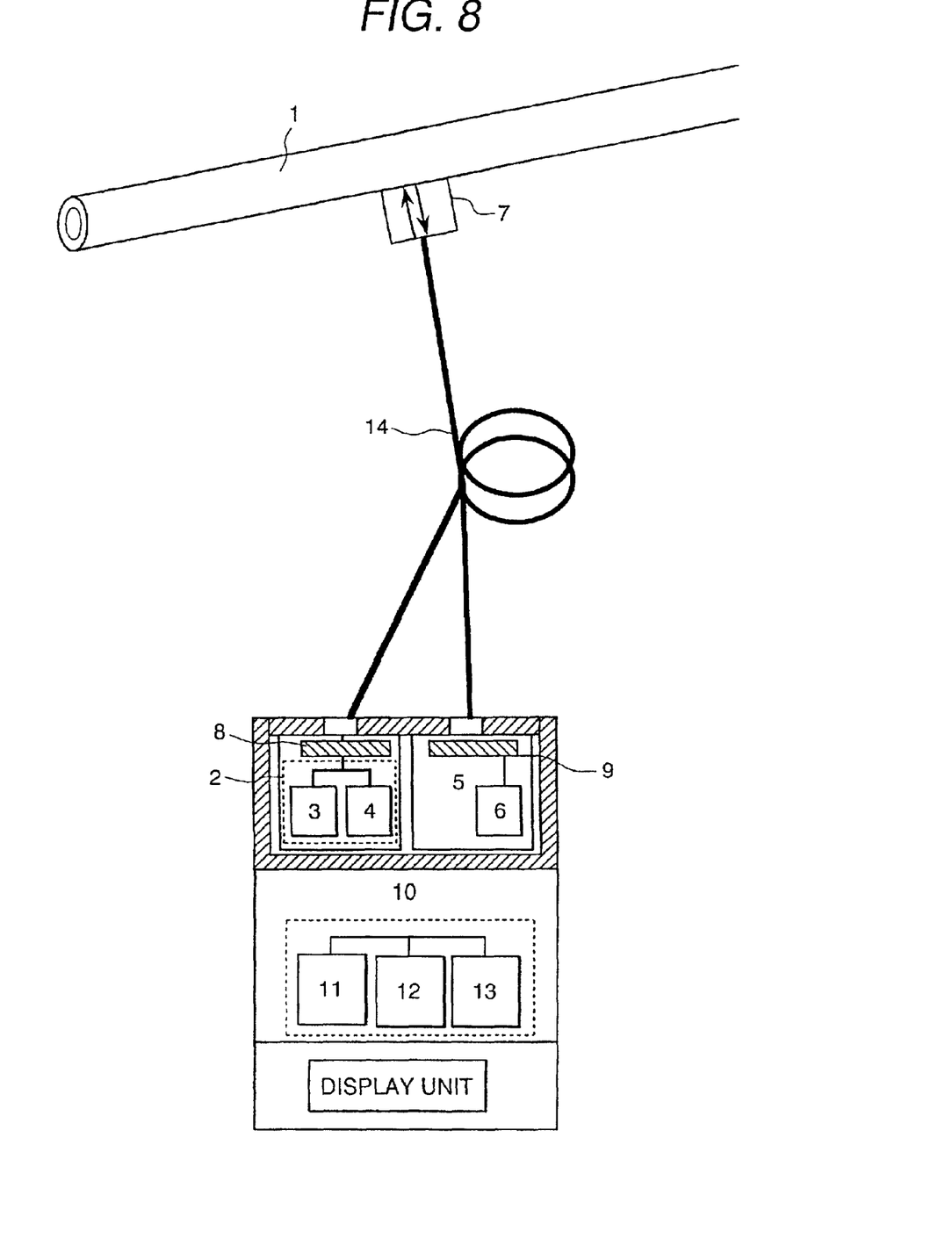
FIG. 8 is a block diagram showing an embodiment of a non-destructive diagnosis system for cable sheathing insulation material (using an optical fiber cable) in accordance with the present invention.
Figure 9:
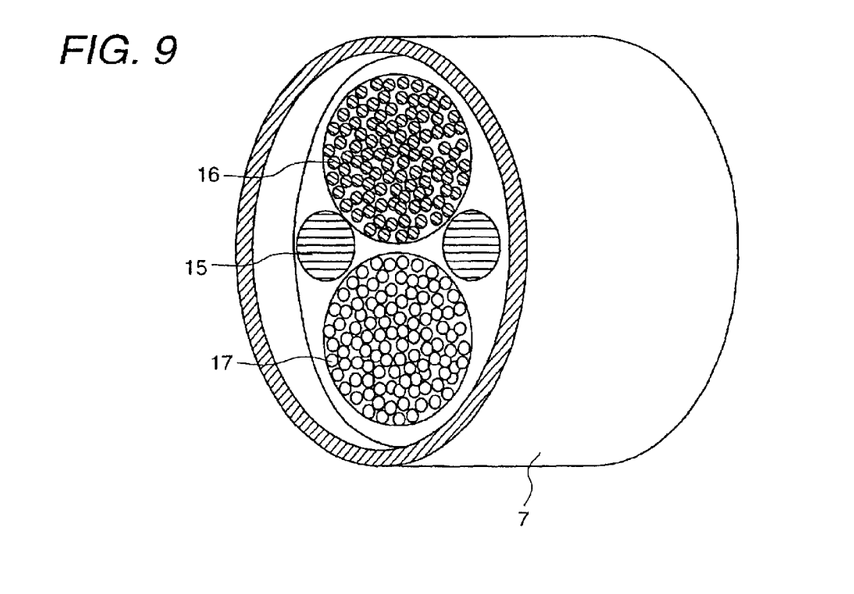
FIG. 9 is a view showing the structure of an end face of the optical fiber cable.

Description will be made below on the method of evaluating the depolarization degree (DP) of the polarized light by measuring polarized light of the reflected light of the cable coating insulation material 1, referring to FIG. 8. Firstly, the operation part 12 outputs an instruction of inserting the polarizer 8 and the analyzer 9 to insert filters to the light source portion 2 and a detector 6. A rotating mechanism for detecting a rotation of a plane of polarization due to the measured sample is contained in the analyzer 9, and the operation part 12 also executes driving control of the rotating mechanism. As shown in FIG. 9, polarization plane conservation fiber was used for the optical fiber cables. In the present embodiment, light measurement using the light source of λ2 was performed. In order to determine a reference angle $\alpha_0$, before starting actual measurement, pre-measurement is performed using an alumina white plate or the like and, the result is pre-set to the operation part. The polarized emitted light from the light source of λ2 is reflected on the surface of the cable coating insulation material 1 to reach the detector 6 through the analyzer 9. The analyzer is driven by a servo motor until the quantity of light becomes the maximum value, and the angle α and the light intensity $I_\alpha$ at that time are obtained. Therein, a distance between the surface of the cable coating insulation material 1 and the end surface (including a protective quartz glass plate) of the light source portion 2 is 2.5 mm. Next, the analyzer 9 is rotated to a position of an angle larger than α by +90° to measure a light intensity $I_{90}$ at that position. In the present invention, $I_{ratio}=I_{90}/I_\alpha$ is used as the index of DP. The first deterioration degree is determined from the value $I_{ratio}$ obtained as described above. The measured result in this time was $I_{ratio}$=0.18. Further, a relationship (a master curve) between the depolarization degree (DP) of the polarized light and the deterioration degree of the cable coating insulation material 1 shown in FIG. 5 is pre-stored in the operation part 12, the measured deterioration degree of the cable coating insulation material can be calculated as the reduced time θ using the relational chart to display the result. Since the ratio $I_{ratio}$ at the lifetime point in the case of the cable coating insulation material in this time is 0.24, the progress degree of the deterioration is 75%.

Figure 7:
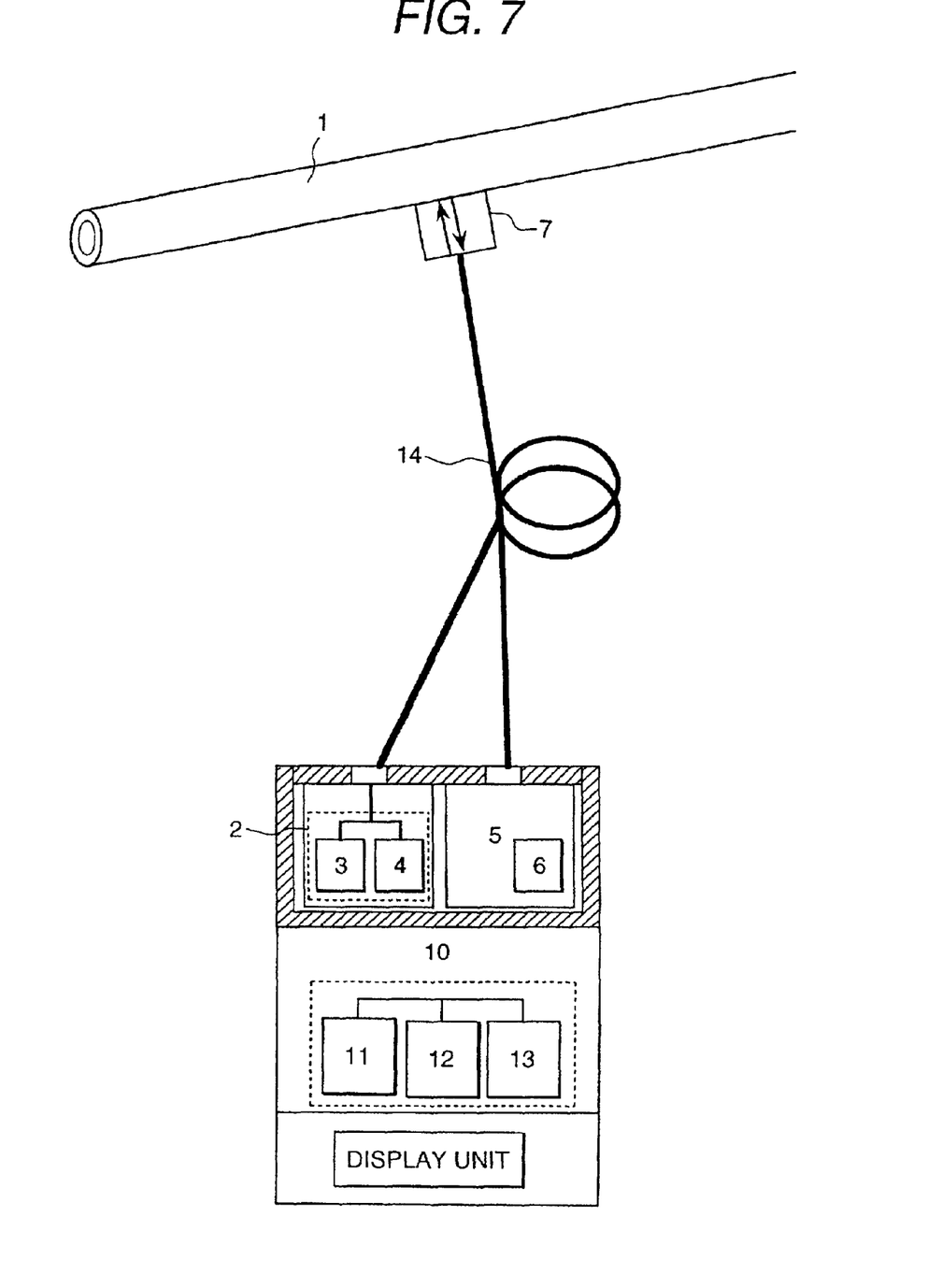
FIG. 7 is a block diagram showing an embodiment of a non-destructive diagnosis system for cable sheathing insulation material (using an optical fiber cable) in accordance with the present invention.

Next, description will be made below on the method of evaluating the absorbance difference or the absorbance ratio by measuring light intensities of the reflected light of the cable coating insulation material 1, referring to FIG. 7. The reflected light intensities ($I_{\lambda 1}$, $I_{\lambda 2}$) of the cable coating insulation material 1 of the light sources of the individual wavelengths were measured as flows. The emitted light from the light source of λ1 is reflected on the surface of the cable coating insulation material 1 to reach the light quantity measuring portion 5, and the light intensity $I_{\lambda 1}$ is obtained. Therein, a distance between the surface of the cable coating insulation material 1 and the end surface (including a protective quartz glass plate) of the light source portion 2 is 2.5 mm. There, the optical fiber cable is composed of a bundle of multi-component glass optical fibers, and the outer diameter of the bundle is 0.5 mm and the length of the optical fiber is 1 m. An optical system is set so that the irradiating light beams of the two wavelengths of λ1 and λ2 emitted from the light source portion 2 are irradiated onto the same area on the surface of the cable coating insulation material 1. The operation part 11 calculates the reflection absorbance in the wavelength λ1 using Equation (1) to store $A_{\lambda 1}$. Therein, the reference reflection light intensity $I_0$ for each wavelength has been measured using an alumina white plate and pre-set to the operation part before starting the measurement. Similarly, the reflection light intensity $I_{\lambda 2}$ of the cable coating insulation material 1 to the emitted light from the light source λ2 is measured, and the reflection absorbance $A_{\lambda 2}$ for the light of wavelength λ2 is stored in the operation part 11. The reflection absorbance difference ΔA between the two wavelengths is calculated from the values of reflection absorbance $A_{\lambda 1}$ and $A_{\lambda 2}$ of the cable coating insulation material 1 to the wavelengths λ1 and λ2 using Equation (2). Since the measured results in this time were $I_{0,\lambda 1}$=1.26 μW, $I_{0,\lambda 2}$=0.98 μW, $I_{\lambda 1}$=0.52 μW and $I_{\lambda 2}$=0.66 μW, the reflection absorbance difference ΔA became 0.213 from Equation (1) and Equation (2). Further, a relationship (a master curve) between the reflection absorbance difference and the deterioration degree of the cable coating insulation material 1 shown in FIG. 4 is pre-stored in the operation part 11, the measured deterioration degree of the cable coating insulation material can be calculated as the reduced time θ using the relational chart to display the result. Since the reduced time $0\theta_0$ at the lifetime point in the case of the cable coating insulation material in this time is 0.30, the progress degree of the deterioration is 71%.

Finally, in the operation part 13, the comprehensive deterioration degree of the cable coating insulation material 1 is determined from the first deterioration degree (75%) and the second deterioration degree (71%) obtained as described above based on a pre-stored relationship. The present embodiment employed a relational equation which determines a value of the further progressed deterioration degree as the comprehensive deterioration degree in the safety side by comparing the first deterioration degree and the second deterioration degree. As the result, the value of the first deterioration degree (75%) is obtained as the final result of the deterioration degree. That is, when the higher structure (crystallization degree) change and the chemical structure (bonding form) change are evaluated in the factor-by-factor basis, it can be judged that in the cable coating insulation material, progress of the deterioration caused by the higher structure (crystallization degree) change is large. As described above, it is possible to perform comprehensive diagnosis capable of including change in values of the other physical properties which have failed to be noticed by the conventional evaluation technologies paying attention on only one physical property. As described above, in the present invention the deterioration degree can be diagnosed on each deterioration basis.

In a case of diagnosing a cable insulator, the diagnosis can be performed using the cable insulator instead of the cable coating insulation material 1.

Further, a cable formed by bundling several cables coated with a coating insulation material and further sheathing the bundled cables with a cable sheath is widely used for various kinds of products. In deterioration diagnosis for the cable of this kind, deterioration of the inside cable coating insulation material may be estimated by diagnosing the cable sheath. However, it is preferable that the cable coating insulation material is directly diagnosed in a portion where the cable sheath has been pealed off.

(Embodiment 3)

Figure 10:
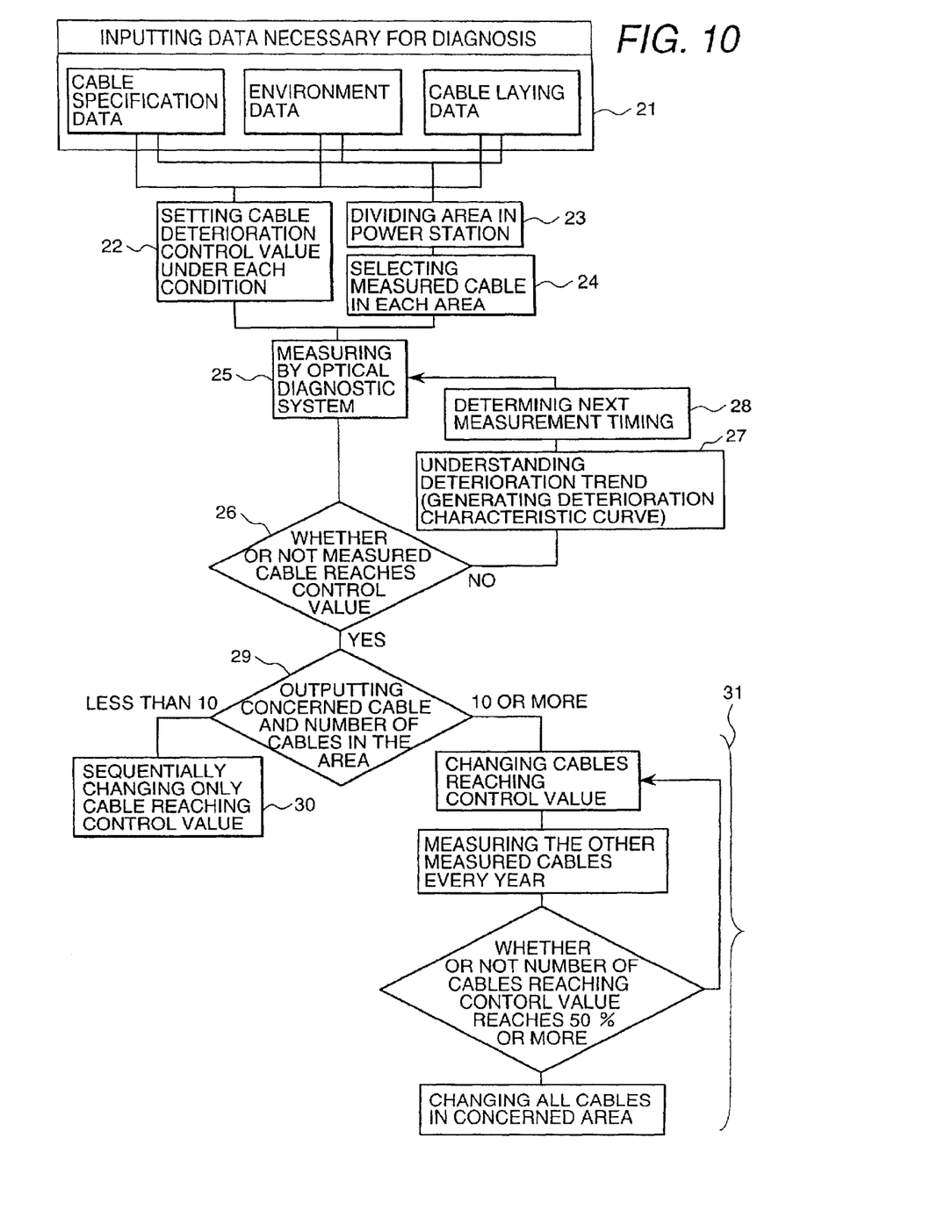
FIG. 10 is a cable deterioration manage flowchart in accordance with the present invention.

An embodiment of a cable deterioration management method will be described below. FIG. 10 is a flowchart showing a flow of cable deterioration management.

Firstly, data necessary for performing the deterioration management and the deterioration diagnosis is input to a database. As the data, cable specification data, environment data and cable laying data are input.

The cable specification data is composed of information on insulation materials and data expressing the correlation between a deterioration degree of the insulation material and a measured value. The cable insulation material is different depending on the kind of cable, and the deterioration rate is also different depending on the material. Therefore, the insulation material information and the data on the previously obtained master curve for each of the material are input as the cable specification data.

The environment data means data expressing a surrounding environment of the cable. For example, since the insulation material is deteriorated by being affected by a surrounding environment condition (temperature, radiation), the environment conditions (temperature, radiation dose) are important. Further, it is possible to output a characteristic curve under an environment from a master curve for a relating cable using the conditions. Information on an environment under which each of the cables is laid, and information expressing correlations among deterioration of the cable under the environment and a measured value, time etc. are input as the environment data.

The cable laying data means data expressing a laying status of a cable. It is difficult to measure and manage all cables because a large amount of cables are laid in a power station. Further, the environment condition of a single cable is different depending on the laying route, and the deterioration rate of the single cable is also different area-by-area. Further, it is necessary for predicting deterioration to input information on a laying time of a relating cable. The various kinds of information described above are input as the cable laying data.

The above is Step No.21 in the flowchart.

Next, a control value of a cable is set. In regard to the control value, a time point slightly before a lifetime of a cable is set as the control value.

The lifetime of a cable is set depending on the using condition of the corresponding cable.

Since a cable for a safety system is required to operate during a loss-of-coolant accident (LOCA), the lifetime of the safety system cable is set to a time point that the safety system cable is deteriorated so as to be unable to withstand a LOCA test condition. On the other hand, the lifetime of a cable for a general system is set to a time point that cracks occurs in the insulation material. Setting of the lifetime is not limited to the above, and lifetime may be changed case by case. For example, lifetime may be defined as a time point that an absolute value of elongation of an insulation material reaches 50%, as generally used.

Next, the control value of a cable is set to a time point capable of changing the cable before the cable reaches the lifetime. Although the control value is set according to a changing time period by taking the physical amount of corresponding cables, the laying status and the priority into consideration, the control value may be managed using the deterioration degree (%) from the initial value as shown in Embodiment 1, or may be managed using the absolute value of elongation (%) of the insulation material.

In a case of a nuclear power plant, the scheduled inspection is performed once a year, and cable changing is performed during that period. The control value is basically set at the timing three years before a timing of the lifetime including the implementation of changing and the prior site survey. However, if it is difficult to complete the changing work during one scheduled inspection period due to the physical amount of cables in an area, the laying status and so on, the control value considering three years or more may be set. The above is Step No.22.

The various kinds of information are read out from the database, and the inside of the power station is divided into a plurality of areas according to the environment conditions. Then, the physical amounts of cables (each cable kind, use) in each of the areas are arranged. This process is Step No.23.

Figure 11:
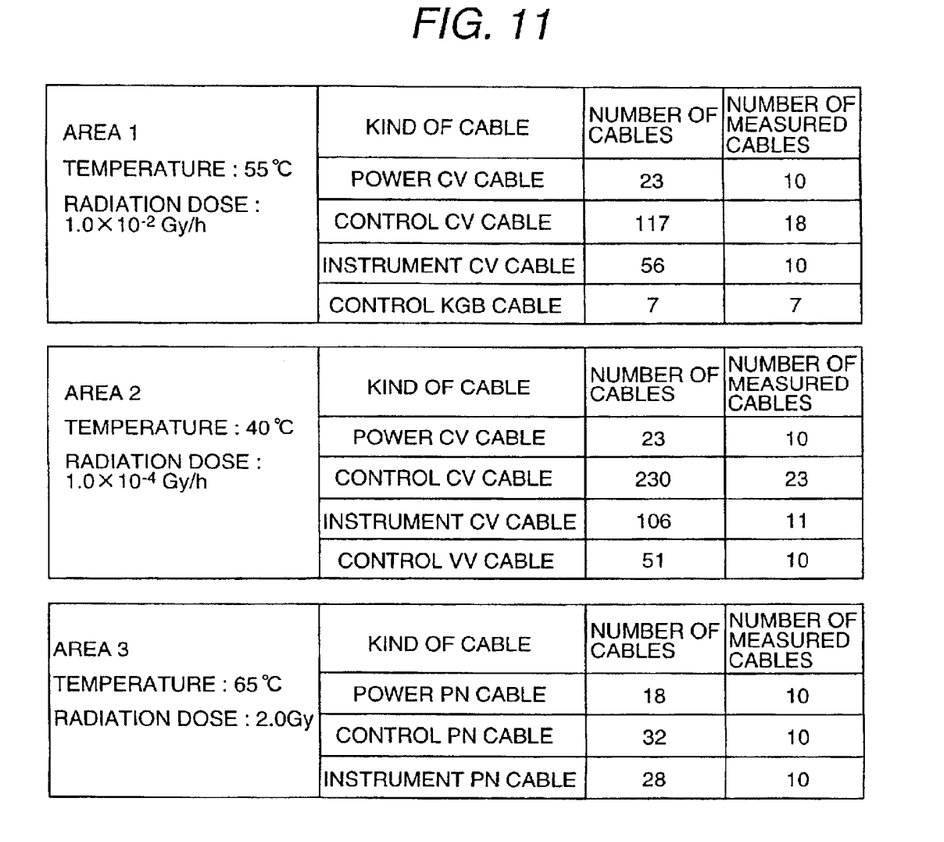
FIG. 11 is a diagram showing an example of amount of cables and selection of number of cables to be measured in each area divided according to environmental condition in a power station.

If the physical amount of cables in one area divided in Step 23 is less than 10 cables, all the cables in the area are determined to be measured. If the physical amount of cables in one divided area is more than 10 cables, 10% of the total physical amount and 10 cables in minimum are determined to be measured. The cables to be measured are selected in place so that the condition of the total region of the area can be expressed by the selected cables, and the cable numbers are recorded, and after that time the selected cables will be continued to be measured. FIG. 11 shows an example of cable selection. The cables selected as described above are input to the database as initial data for executing the non-destructive diagnosis. The above is Step No.24.

In the power station, measurement is performed to the selected cables in each of the areas according to the method of Embodiment 1. The above is Step No.25.

In Step No.26, the measured value is compared with the control value previously set. If the measured value does not reach the control value, the data is recorded and the measurement is to be performed again during the next scheduled inspection.

Although the non-destructive diagnosis of the cable is periodically performed until the measured value reaches the control value, the measured data is used for generating a deterioration characteristic curve in order to understanding the deterioration trend. This is Step No.27.

The next measurement implementation timing is determined according to a decreasing rate of the deterioration degree from the initial value. The measurement is performed every five years until the deterioration degree reaches a value smaller than 50% of the initial value. After the deterioration degree reaches a value lager than 50% of the initial value, the measurement is performed every three years. The above is Step No.28.

If the measured result reaches the control value, number of cables in the area relating to the measured cables is output in order to perform different management method depending on the number of cables. This work is Step No.29.

If the number of cables is equal to and smaller than 10, that is, all the cables are measured, the cables reaching the control value are sequentially changed one by one. This is Step No.30.

If the number of cables is larger than 10, the cables reaching the control value are changed, and the other measured cables are left as they are and the measurement of the other measured cables is to be performed every year. The deterioration degrees of the measured cables gradually reach the control value. Then, when number of the measured cables reaching the control value reaches one-half of the initial number of the cables to be measured, it is judged that deterioration degrees of all the cables in the area reach the control value, and all the cables in the area are changed. This is Step No.31.

(Embodiment 4)

Figure 12:
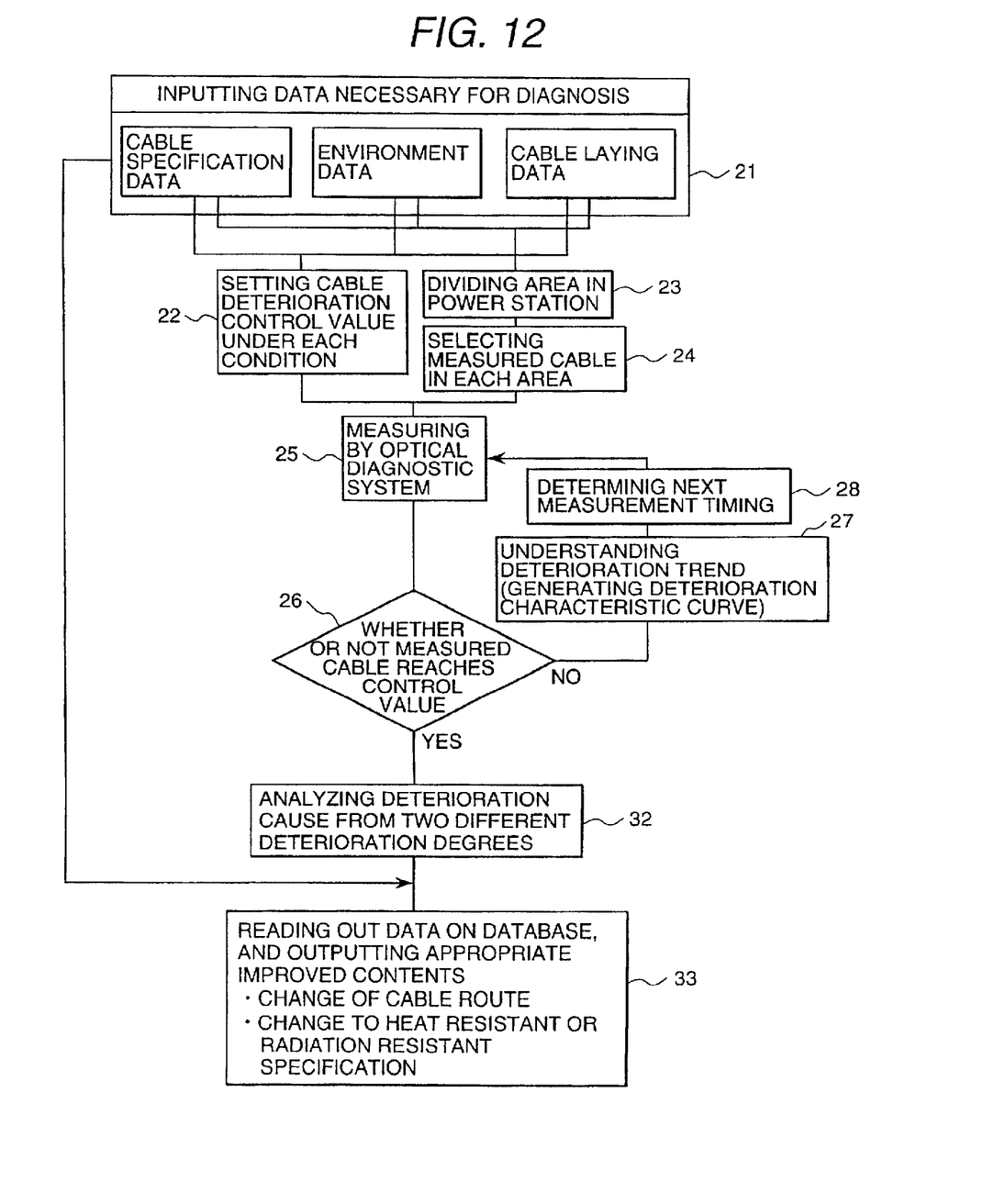
FIG. 12 is a management flowchart in accordance with the present invention which analyzes a deterioration factor from deterioration form and outputs improved contents.

FIG. 12 shows a management flow in the cable deterioration management method in which deterioration factors are analyzed from the deterioration forms to output improved contents.

The program is formed in such that when the deterioration degree reaches the control value in Step No.26 of Embodiment 3, a ratio of the deterioration forms (oxidation, principle-chain cut and so on) of the cable is analyzed from the two different deterioration degrees and the diagnosed result to judge whether the main factor of the cable deterioration is caused by heat or radiation ray. The above is Step No.32.

There, improved contents for moderating the deterioration factor are output using the cable specification data, the cable laying data in the database on Step No.21. For example, in a case where it is judged that the deterioration of the cable is caused mainly by heat, a command which recommends using a heat resistant cable is output when a general cable has been used, or a command which recommends changing the route of the cable when there is a heat source such as a high-temperature pipe near the laying place of the cable. The above is Step No.33.

(Embodiment 5)

Description will be made below on a method of diagnosing a deterioration degree from a depolarization degree of polarized light by measuring polarization of reflected light from a crystalline resin material. Here, the deterioration degree of a polyethylene film caused by ultraviolet irradiation will be evaluated. Initially, in order to determine a reference angle $\alpha_0$, before starting actual measurement, the reference direction is measured using an alumina white plate or the like. The analyzer is rotated until the quantity of light becomes the maximum value, and the angle $\alpha$ and the light intensity $I_\alpha$ at that time are obtained. Next, the analyzer is rotated to a position of an angle larger than $\alpha$ by +90° to measure a light intensity $I_{90}$ at that position. In the value $I_{ratio}=I_{90}/I_\alpha$ is used as the index of DP, and the deterioration degree is determined from the value $I_{ratio}$. The determination was executed using the relationship (the master curve) between the depolarization degree (DP) and the deterioration degree which had been separately formed. By doing so, variation in crystallization degree caused by ultraviolet irradiation could be measured.

(Embodiment 6)

Description will be made below on a method of diagnosing quality from a depolarization degree of polarized light by measuring polarization of reflected light from a crystalline resin material. Here, the orientation degree of an alignment film coated on a substrate will be evaluated. Initially, in order to determine a reference angle $\alpha_0$, before starting actual measurement, the reference direction is measured using an alumina white plate or the like. The analyzer is rotated until the quantity of light becomes the maximum value, and the angle $\alpha$ and the light intensity $I_\alpha$ at that time are obtained. Next, the analyzer is rotated to a position of an angle larger than $\alpha$ by +90° to measure a light intensity $I_{90}$ at that position. In the value $I_{ratio}=I_{90}/I_\alpha$ is used as the index of DP, and the orientation degree is determined from the value $I_{ratio}$. The determination was executed using the relationship (the master curve) between the depolarization degree (DP) and the deterioration degree which had been separately formed. By doing so, irregularity in the orientation in the film could be evaluated by measuring the orientation degree of the alignment film while scanning on the alignment film.

(Embodiment 7)

Description will be made below on a method of diagnosing materials from a depolarization degree of polarized light by measuring polarization of reflected light from a crystalline resin material. Here, the properties of paper (common paper, paper for copying, paper for color copying, paper for ink-jet printing, recycled paper, coated paper) will be identified and evaluated. Initially, in order to determine a reference angle $\alpha_0$, before starting actual measurement, the reference direction is measured using an alumina white plate or the like. The analyzer is rotated until the quantity of light becomes the maximum value, and the angle $\alpha$ and the light intensity $I_\alpha$ at that time are obtained. Next, the analyzer is rotated to a position of an angle larger than $\alpha$ by +90° to measure a light intensity $I_{90}$ at that position. In the value $I_{ratio}=I_{90}/I_\alpha$ is used as the index of DP, and the paper property is determined from the value $I_{ratio}$. The determination was executed using the relationship between the depolarization degree (DP) and the paper property which had been separately formed. In this embodiment, all the above six kinds of paper properties could be identified.

What is claimed is:

1. A diagnostic system for diagnosing deterioration of an article comprising:

a light source part for irradiating irradiation light having polarization onto a surface of the article;

a light receiving part for receiving the reflected light from said article;

a measurement part for measuring a variation of polarized light between said irradiation light and said reflected light; and a diagnosing part for diagnosing a deterioration degree of said article from said measured variation.

2. A method of diagnosing deterioration of an article, the method comprising the steps of:

irradiating irradiation light having polarity from a light source emitting light having at least one kind of wavelength onto a surface of said article;

receiving the reflected light from said article;

measuring a depolarization degree of polarized light of said reflected light;

determining a first deterioration degree of said article by executing comparison operation using a pre-stored relationship between depolarization degrees of polarized light and deterioration degrees formed using a deteriorated material of the same kind as a material of said article;

irradiating irradiation light having at least two kinds of wavelengths onto the surface of said article;

receiving the reflected light from said article;

measuring an absorbance difference or an absorbance ratio of said reflected light;

determining a second deterioration degree of said article by executing comparison operation using a pre-stored relationship between absorbance difference or absorbance ratio and deterioration degree formed using a deteriorated material of the same kind as a material of said article; and determining a comprehensive deterioration degree of said article from the determined results of the first deterioration degree and the second deterioration degree based on a pre-stored relationship.

3. A method of managing deterioration of an article using the method of diagnosing deterioration according to claim 2, the method comprising the steps of discriminating a deterioration factor of said article; and outputting improved contents to said factor.

4. A method of diagnosing deterioration of an article according to claim 2, wherein said article is a cable sheathing insulation material.

5. A method of diagnosing deterioration of a cable sheathing insulation material according to claim 4, wherein the deterioration diagnosis of a cable sheathing insulation material is performed using a portion in a state that a cable sheath material is peeled.

6. A method of managing deterioration of a cable sheathing insulation material, the method comprising the steps of:

irradiating irradiation light having polarization onto a surface of the cable sheathing insulation material;

receiving the reflected light from said cable sheathing insulation material;

measuring a variation of polarized light between said irradiation light and said reflected light;

diagnosing a deterioration degree of said cable sheathing insulation material from said measured variation;

obtaining a relationship between at least one of physical property and electric characteristic of each material used for the cable sheathing insulation material and a result obtained from the diagnosing step;

inputting data on the cable sheathing insulation material and manufacturing time of a laid cable having the cable sheathing insulation material to be diagnosed, and laying and environment data such as laying time, a place of the cable laying, a laying period and measuring position information to set a deterioration control value for determining a changing timing for each material of the cable sheathing insulation material using the data group for diagnosis in advance; and determining a changing timing of said cable by executing a comparison operation between an optical diagnosis result of the cable sheathing insulation material of said cable to be diagnosed and the preset deterioration control value.

* * * * *